United States Patent [19]
Crane

[11] 3,968,379
[45] July 6, 1976

[54] PHOTOCELL SMOKE DETECTOR
[75] Inventor: Burke J. Crane, Lombard, Ill.
[73] Assignee: Rixson-Firemark, Inc., Franklin Park, Ill.
[22] Filed: Nov. 29, 1974
[21] Appl. No.: 528,010

[52] U.S. Cl. .............................. 250/574; 250/565; 356/207; 340/237 S
[51] Int. Cl.[2] ........................................ G01N 21/26
[58] Field of Search.... 250/564, 565, 210, 573–575; 356/207; 340/237 S

[56] References Cited
UNITED STATES PATENTS

| | | | |
|---|---|---|---|
| 3,135,950 | 6/1964 | Finkle | 340/237 X |
| 3,417,392 | 12/1968 | Hansen, Sr. et al. | 356/207 X |
| 3,497,303 | 2/1970 | Enemark et al. | 250/574 X |
| 3,524,707 | 8/1970 | Hansen, Sr. et al. | 250/574 X |

Primary Examiner—Walter Stolwein

[57] ABSTRACT

A photocell smoke detector comprising a housing defining a dual section smoke chamber having a first smoke sensing chamber and a second compensating chamber, a smoke sensing photocell coupled to the smoke sensing chamber and a compensating photocell coupled to the second chamber, a light source coupled to the compensating chamber and transmitting a beam of light generally parallel and away from the photosensitive surfaces of the two photocells, and a light trap communicating with the smoke sensing chamber and fabricated of layers of corrugated media sandwiched between relatively flat liners whereby light is absorbed in the flutes of the corrugated media and smoke is enabled to pass freely into and out of the smoke sensing chamber.

5 Claims, 4 Drawing Figures

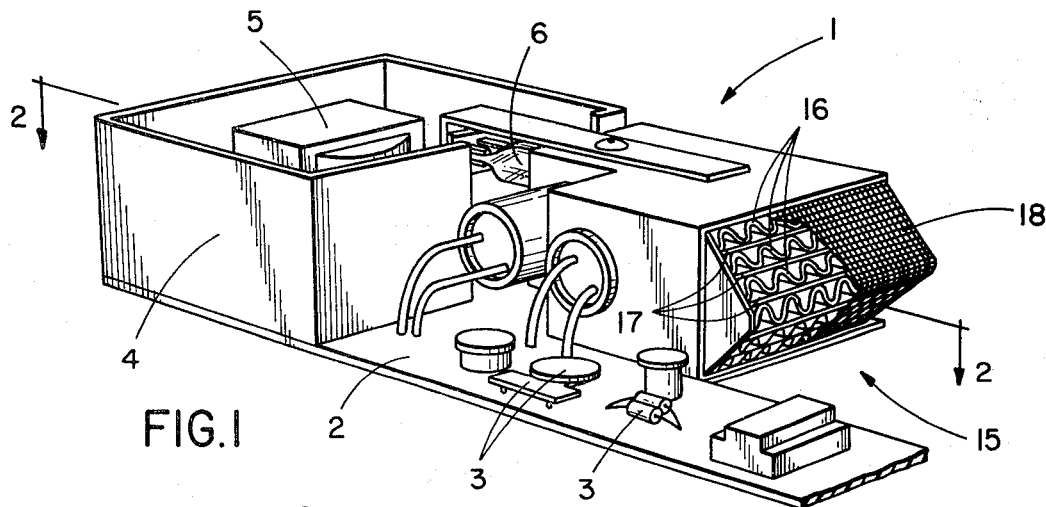

PHOTOCELL SMOKE DETECTOR

BACKGROUND OF THE INVENTION

This invention relates to scatter type smoke detectors. Detectors of this type include an exciter lamp illuminating a chamber in which particulate matter such as smoke is to be detected. A smoke sensing photocell is coupled to the chamber and constantly senses a very low illumination emanating from the exciter lamp. When particulate matter enters the smoke chamber, light is scattered to the cell's photosensitive surface and the cell's light response increases triggering a threshold circuit to operate an alarm.

False alarms may be indicated by the smoke detector in the event excessive ambient light is permitted to enter the smoke chamber or the light emanating from the exciter lamp is not kept at a sufficiently low level.

Accordingly, seemly inconsistent criteria must be satisfied in keeping ambient light, as well as light from the exciter lamp, at a relatively low level; and at the same time, enabling particulate matter, such as smoke, easy access into and out of the smoke detector.

SUMMARY OF THE INVENTION

Accordingly, a principal object of this invention is to provide an improved smoke detector with a highly efficient light trap so that smoke may be readily detected without false alarms rendered by undesired ambient light or changes in exciter lamp light level.

The smoke detector of this invention comprises a dual section smoke chamber, both chambers constructed to prevent ambient light from entering. A photoconductive cell is exposed to the interior of each chamber. A beam of light generated by an exciter lamp is transmitted through each chamber at right angles to the photocells. The first chamber, or compensating chamber, is isolated somewhat from the atmosphere; and the second chamber, or smoke chamber, is freely ventilated through a light trap made up of corrugated cardboard layers.

The two photocells are mounted and shielded so that about the same amount of light impinges upon both photocells under alarm triggering conditions. When smoke is present, the photocell in the smoke chamber is illuminated to a greater extent due to the light reflecting off the smoke particles located in the beam of light. This causes a change in resistance of the smoke sensing photocell.

The photocells are electrically connected in a bridge circuit and any unbalance is amplified and used to control a a relay. The bridge is balanced under normal conditions and the change of resistance of the smoke detecting photocell due to smoke unbalances the bridge. The electrical signal output from the unbalanced bridge may then be amplified by conventional circuitry to actuate an audible alarm or a door control.

DETAILED DESCRIPTION OF THE DRAWINGS

In order that all of the structural features for attaining the objects of this invention may be readily understood, reference is herein made to the accompanying drawings wherein:

FIG. 1 is a perspective view of the smoke detector module of this invention including some of the associated amplifier and relay circuitry components as used in an alarm system;

FIG. 2 is a section view taken along line 2—2 of FIG. 1 showing in elevation the light ray emanating from the exciter lamp light source as it traverses through a dual section smoke chamber and is absorbed in the light trap;

FIG. 3 is a section view showing a plan view of the light ray generated by the exciter lamp light source; and FIG. 4 is a simplified schematic drawing showing the interconnection of the photocells of the smoke detector in a smoke alarm bridge circuit.

DETAILED DESCRIPTION OF THE PREFERRRED EMBODIMENT

Referring now to the drawings, a smoke detector 1 is shown supported on circuit board 2 which carries a plurality of amplifier and other circuit components 3, the details of which are not significant to the invention. Additionally, circuit board 2 carries a wall enclosure 4 within which transformer 5 and exciter lamp 6 are housed.

Exciter lamp 6 is supported on a metallic bracket 7 (FIG. 2) which is affixed (in a manner not shown) to a plastic smoke detector housing 8 for photocell smoke detector 1. Housing 8 defines a compensating chamber 9 and a smoke sensing chamber 10. As is viewed in FIG. 2, wall 11 of housing 8 is formed with an exciter lamp aperture 12. The right end of the lamp 6 envelope is tightly fit within aperture 12 and is carried in this position by bracket 7, so that the energization of the lamp filament illuminates compensating chamber 9, generally in accordance with triangular broken-line light-ray configuration 13 shown in FIG. 2.

It should be noted that dividing wall 14, which separates compensating chamber 9 and smoke sensing chamber 10, is also formed with a circular light transmitting aperture 34 which is in the light-ray path 13 emanating from exciter lamp 6. Ultimately light ray 13 is absorbed in a light trap 15 which is fabricated of a plurality of corrugated media 16, separated and sandwiched between flat liner sheets 17.

In a preferred embodiment, light trap 15 is fabricated of corrugated cardboard elements which comprise the corrugated media and also the liner sheets. All of these elements are preferably coated with a flat black coating so that optimum light absorption occurs in the passageway defined by the flutes of the corrugated media 16 and the liner strips 17.

As is best shown in FIGS. 1 and 3, the light trap 15 has a relatively V-shaped cross section whereby the trap is tapered to a generally projecting line at its midsection. This tapered configuration enables easier access to smoke sensing chamber 10 through the openings defined by the flutes of the corrugated media 16. Similarly, this configuration also enables smoke easier egress through the light trap after it has passed through smoke sensing chamber 10.

In operation, smoke may enter either from the flute openings from above the centermost liner sheets 17 or below these flute openings. In either case, ultimately the smoke will pass through the smoke sensing chamber 10 and ultimately out of the light trap into ambient atmosphere.

In order to prevent false operation of the smoke detector 1 due to small insects, or the like, entering smoke sensing chamber 10 and simulating smoke, the outer flute openings of light trap 15 should be covered with a wire screen cover 18, as is shown only in FIG. 3.

Light compensating photoconductive cell 19 is optically coupled to compensating chamber 9 by means of enlarged passageway 20 and smaller aperture 21. The light compensating photocell 19 is partially hermetically sealed by means of rubber gasket 22 which envelopes the connection terminals of the light compensating photocell. Similarly, smoke sensing photocell 23 is optically coupled to smoke sensing chamber 10 by means of enlarged passageway 24. As is viewed in the cross-sectional view of FIG. 2, the passageway has a tapered end and light access may be had only through hemispherical opening 25, as is best shown in FIG. 3. The cross sectional tapering of the enlarged passageway 24 in the manner shown in FIG. 2, minimizes the ambient light which may strike the photoconductive surface of smoke sensing photocell, thereby improving the reliability and sensitivity of the smoke detector. Smoke sensing photocell 23 is similarly isolated within its socket opening by means of rubber gasket 26.

In an operating circuit configuration (FIG. 4), photoconductive compensating cell 19 and photoconductive smoke sensing photocell 23 are connected in a bridge circuit with potentiometers 27 and 28, and normally balanced so that the input to amplifier 29 is below the threshold value. Compensating photocell is included in the circuit so that changes in light intensity from exciter lamp 6, aging of the photocells, etc. are compensated for in a conventional manner so as not to result in a false alarm. In the event that smoke entering light trap 15 makes its way into smoke sensing chamber 10, the light rays 13 emanating from exciter lamp 6 will be scattered so as to pass through enlarged passageway 24, thereby reducing the conductivity of smoke sensing photocell 23 and unbalancing the bridge circuit of FIG. 4. With this circuit occurrence, relay 30 is energized, thereby closing contact 31 and energizing any alarm circuit output device which may be connected to output terminals 32 and 33 of the schematic circuit diagram of FIG. 4.

It should be understood that the structure herein described may be modified without departing from the scope of the invention. For example, the light trap need not be fabricated of corrugated media, but rather any type of divided strips may be inserted between liners 17 so as to form elongated passageways.

What is claimed is:

1. A photocell smoke detector comprising a smoke detector housing defining in part a dual section smoke chamber having a first smoke sensing chamber and a second compensating chamber, with a smoke sensing photocell coupled to the smoke sensing chamber and a compensating photocell coupled to the second chamber, a light source coupled to the compensating chamber and transmitting a beam of light generally parallel and away from the photosensitive surfaces of the two photocells, a dividing wall containing a relatively small light transmitting aperture dividing the smoke sensing and the compensating chambers, and a light trap also defining part of the smoke sensing chamber fabricated of a plurality of layers of corrugated media sandwiched between relatively flat parallel liners whereby light is absorbed in the flutes of the corrugated media and smoke is enabled to pass freely into and out of the smoke sensing chamber while being restricted from entry into the compensating chamber by the dividing wall.

2. The combination of claim 1 in which the flat liners and the defined flute openings are generally parallel to the longitudinal axis of the beam of light.

3. The combination of claim 1 in which the light trap has a relatively V-shaped cross-section whereby the trap is tapered to a generally projecting line at its midsection which enables smoke easier access to and egress from the light trap.

4. A photocell smoke detector comprising a smoke detector housing defining in part a dual section chamber having a first smoke sensing chamber and a second compensating chamber, a smoke sensing photocell coupled to the smoke sensing chamber and a compensating photocell coupled to the second chamber, a light source coupled to the compensating chamber and transmitting a beam of light generally displaced from the photosensitive surfaces of the two photocells, a dividing wall containing a relatively small light transmitting aperture dividing the smoke sensing chamber and the compensating chamber, and a light trap also defining part of the smoke sensing chamber fabricated to provide a plurality of elongated grid-like openings whereby light is absorbed in the grid-like openings and smoke is enabled to pass freely into and out of the smoke sensing chamber through the grid openings while being restricted from entry into the compensating chamber by the dividing wall.

5. The combination of claim 4 in which the light trap has a relatively V-shaped cross-section projecting from the housing whereby the trap is tapered to a generally projecting line at its midsection which enables smoke easier access to and egress from the light trap by passing substantially entirely through the smoke sensing chamber only.

* * * * *